(12) United States Patent
Gordon et al.

(10) Patent No.: US 8,991,502 B2
(45) Date of Patent: Mar. 31, 2015

(54) SAMPLING ASSEMBLY FOR A WELL

(75) Inventors: Alexandre Gordon, Aberdeen (GB);
Duncan James Trinder, Aberdeenshire (GB)

(73) Assignee: Cameron International Corporation, Houston, TX (US)

( * ) Notice: Subject to any disclaimer, the term of this patent is extended or adjusted under 35 U.S.C. 154(b) by 264 days.

(21) Appl. No.: 13/460,008

(22) Filed: Apr. 30, 2012

(65) Prior Publication Data
US 2013/0284443 A1 Oct. 31, 2013

(51) Int. Cl.
| E21B 43/01 | (2006.01) |
| E21B 49/08 | (2006.01) |
| G01N 1/14 | (2006.01) |
| G01N 1/20 | (2006.01) |

(52) U.S. Cl.
CPC .................. *E21B 49/08* (2013.01); *G01N 1/14* (2013.01); *G01N 2001/2071* (2013.01)
USPC ........... 166/344; 166/345; 166/338; 166/341; 166/264; 166/250.01

(58) Field of Classification Search
USPC ......... 166/345, 338, 344, 347, 351, 352, 366, 166/368, 250.01, 264, 369, 373
See application file for complete search history.

(56) References Cited

U.S. PATENT DOCUMENTS

| 3,987,638 | A | * | 10/1976 | Burkhardt et al. | 405/203 |
| 5,730,551 | A | * | 3/1998 | Skeels et al. | 405/170 |
| 6,435,279 | B1 | * | 8/2002 | Howe et al. | 166/336 |
| 8,381,578 | B2 | * | 2/2013 | Sweeney | 73/49.1 |
| 8,430,168 | B2 | * | 4/2013 | Goodall et al. | 166/336 |
| 2009/0288836 | A1 | * | 11/2009 | Goodall et al. | 166/336 |
| 2010/0059221 | A1 | * | 3/2010 | Vannuffelen et al. | 166/264 |
| 2010/0089126 | A1 | * | 4/2010 | Sweeney | 73/40 |
| 2011/0005765 | A1 | * | 1/2011 | Cumming et al. | 166/344 |
| 2012/0000665 | A1 | * | 1/2012 | Omvik | 166/351 |
| 2013/0025874 | A1 | * | 1/2013 | Saunders et al. | 166/357 |

FOREIGN PATENT DOCUMENTS

WO 2010106499 A1 9/2010

OTHER PUBLICATIONS

International Search Report and Written Opinion dated Aug. 20, 2013 for PCT Application No. PCT/US2013/037746 filed Apr. 23, 2013.

* cited by examiner

*Primary Examiner* — James G Sayre
(74) *Attorney, Agent, or Firm* — Chamberlain Hrdlicka (57) ABSTRACT

A sampling assembly for taking single or multiphase production fluid samples from a subsea well. The sampling assembly includes a receiving structure that houses a saver sub and a retrievable skid. The sampling assembly allows for repeated retrieval of collected samples and replenishment of empty sample chambers using the retrievable skid. A releasable connection interface between the retrievable skid and the saver sub allows an ROV to connect the retrievable skid to the saver sub and provide electrical and hydraulic power to the sampling assembly for taking samples.

21 Claims, 13 Drawing Sheets

SAMPLING ASSEMBLY FOR A WELL

BACKGROUND

During the lifespan of an oil reservoir, samples from the reservoir can be collected and analyzed. To effectively sample the production fluid from a well, and more particularly a subsea well, sampling systems are often located in close proximity to the wellhead. Wellhead sampling presents a challenge due to the potential for dispersed and mist flow from the wellhead containing both liquid and gas phases (multiphase flow). To take a liquid sample, the liquid phase must be separated from the gas phase. Multiphase flows exhibiting a dispersed or mist flow regime can be difficult to separate into component liquid and gas phase flows, in turn making the collection of liquid-only samples more difficult.

Further, sample systems may use a flow device, such as a venturi or an orifice plate, to generate a pressure differential proportional to the production flow. If the production flow rate is too low, the pressure differential generated by the flow device may be insufficient to retain a sample that contains both liquid and gas.

Further, multiple samples may be taken during the life of the well. Connecting and unconnecting equipment can be time consuming and servicing connections permanently mounted on the wellhead or other subsea structure can be difficult.

SUMMARY

An oil or gas well and related sampling assembly of this disclosure can be used to sample production fluids from the oil or gas well. The assembly includes a receiving structure that houses a saver sub, a retrievable skid, and protection plates. The receiving structure can be fixably attached to a manifold, an Xmas tree, or a length of pipe from which samples will be taken. The saver sub accesses the production flow via its connection with the receiving structure and then releasably connects with the retrievable skid. The receiving structure allows production fluid samples to be taken throughout the lifecycle of the manifold and the saver sub reduces the number of makes and breaks on the couplings in the manifold—instead, the interface between the retrievable skid and the saver sub is cycled with every sample taken. Among other valves and couplings, the retrievable skid houses the sample collection chambers.

Once the samples have been collected, a remotely operated vehicle (ROV) removes the retrievable skid and brings it to the surface. After the sample chambers are emptied and replaced, the sampling bottles are placed back in the retrievable skid, returned subsea, and reinstalled in the sampling system.

BRIEF DESCRIPTION OF THE DRAWINGS

For a detailed description of the preferred embodiments of the invention, reference will now be made to the accompanying drawings in which.

DETAILED DESCRIPTION

The following discussion is directed to various embodiments of the invention. The drawing figures are not necessarily to scale. Certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed below may be employed separately or in any suitable combination to produce desired results. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function.

In the following discussion and in the claims, the terms "including" and "comprising" are used in an open-ended fashion, and thus should be interpreted to mean "including, but not limited to . . . ." Also, the terms "couple," "connect," "engage," and "attach" are intended to mean either an indirect or direct connection. Thus, if a first device couples to a second device, that connection may be through a direct connection, or through an indirect connection via other devices, components, and connections. The term "fluid" may refer to a liquid or gas and is not solely related to any particular type of fluid such as hydrocarbons. The term "pipe," or the like refers to any fluid transmission means.

Figure 1:
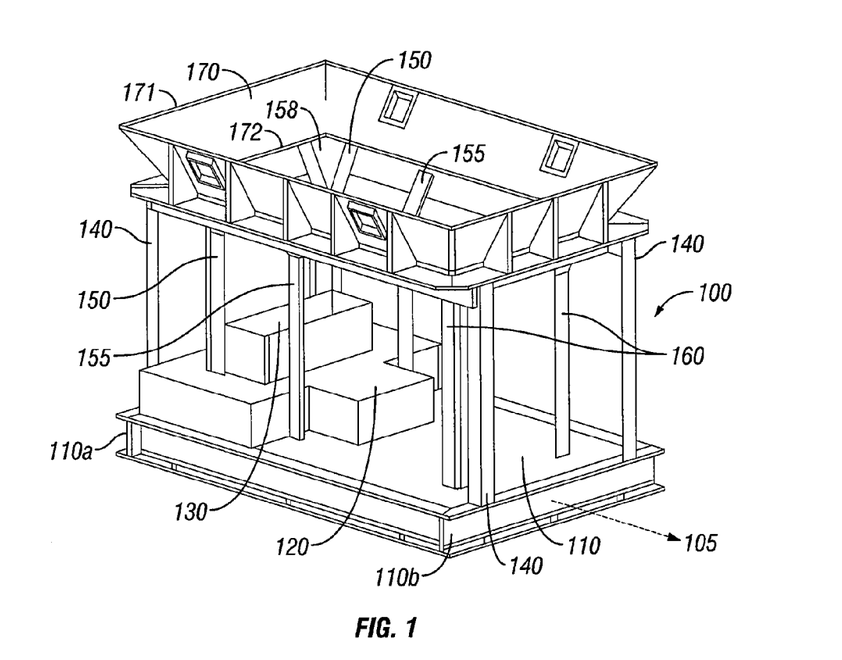
FIG. 1 shows a perspective view of a receiving structure in accordance with various embodiments.

FIG. 1 shows the receiving structure 100, comprised of a base platform 110, a saver sub interface 130, a plurality of posts 140, and a sloped top structure 170. The base platform 110 is generally rectangular but may be configured in any suitable shape. The posts 140 extend from and connect the base platform 110 to the sloped top structure 170. The sloped top structure 170 includes sides that slope inward toward the center of the base platform 110, creating upper perimeter 171 and lower perimeter 172; the upper perimeter being larger than the lower perimeter. In a preferred embodiment, the angle of the sloped top structure 170 is between thirty degrees and sixty degrees.

Two middle saver sub guides 155 extend from the surface of the base platform 110. The middle saver sub guides 155 bend outward toward the lower rectangular perimeter 172 such that the upper portion of the middle saver sub guides 155 is angular and disposed on the lower rectangular perimeter 172. Two corner saver sub guides 150 are disposed on the surface of the raised platform 120. Two corner retrievable skid guides 160 are disposed on the surface of the base platform 110. Each of the four corner guides (2-saver sub guides 150, 2-retrievable skid guides 160) are made up of two middle saver sub guides 155 positioned orthogonally next to each other such that the lower portions of the guides contact each other, forming an "L" shape. A triangular web 158 bridges the gap between the top angular portions of the guides. The top portions of the corner guides 150, 160 bend outward toward the lower rectangular perimeter 172 such that the triangular web 158 and upper portion of guides 150, 160 are angular and disposed on the lower rectangular perimeter 172.

The raised platform 120 is disposed on the surface of the base platform. The raised platform 120 may be rectangular in shape with two corners cut out on the side toward the center of the base platform 110; the two cut outs allowing the middle saver sub guides 155 to attach to the surface of the base platform 110. The saver sub interface 130 is disposed on the surface of the raised platform 120 and houses various components (not shown) for interfacing with the saver sub.

Figure 2:
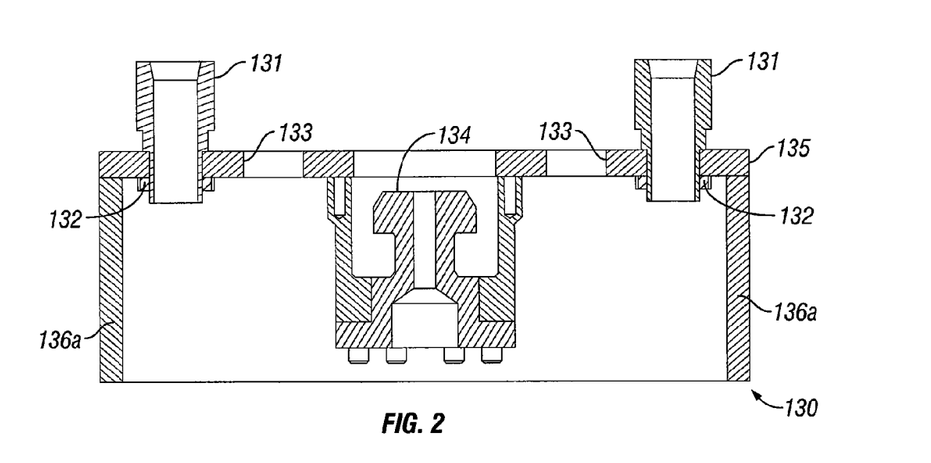
FIG. 2 shows a cross-sectional view of the saver sub interface on the receiving structure.

FIG. 2 shows a cross-sectional view of the saver sub interface 130, which includes: a top plate 135, side walls 136a, and the multiple quick connect (MQC) mating components. The MQC components include: bushing guides 131, a lockdown housing 134, and two pass through holes 133. The MQC allows production fluid to be communicated between the manifold and saver sub (to be described in more detail below). The lockdown housing 134 is typically located in the center of the top plate 135, is cylindrical, and protrudes below the surface of the top plate 135. The lockdown housing 134 attaches with a locking mechanism on the saver sub (to be discussed in more detail below). On either side of the lockdown housing 134 are two pass through holes 133 that accommodate couplings (not shown). On either side of the pass through holes 133 are two bushing guides 131. The bushing guides 131 are secured to the saver sub interface 130 by lock nuts 132, and receive guide pins located on the saver sub (to be discussed in more detail below).

Figure 3:
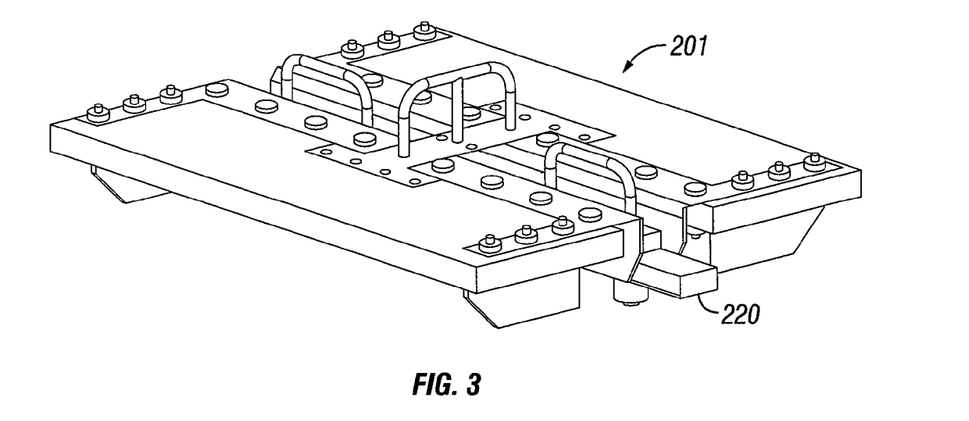
FIGS. 3 and 4 show perspective views of protection plates in accordance with various embodiments.
Figure 4:
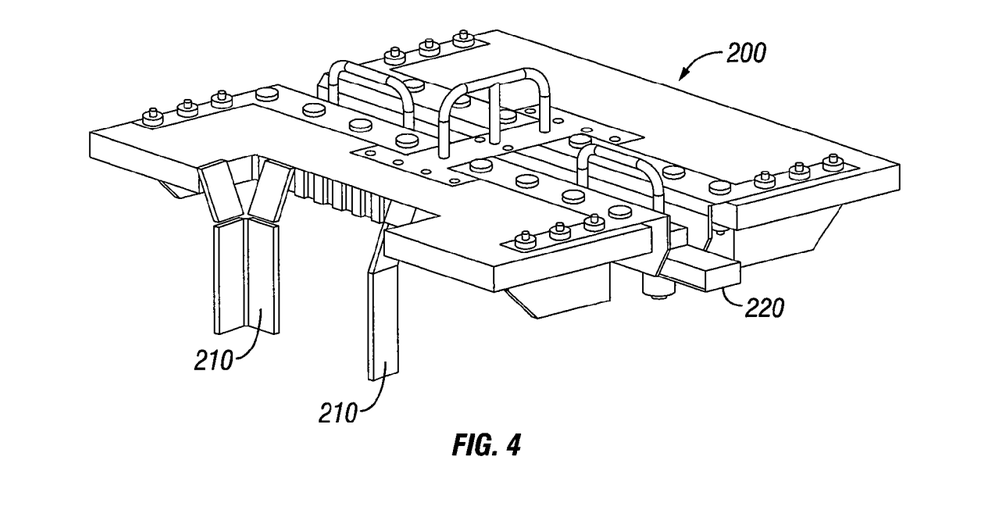

FIGS. 3 and 4 show protection plates 200 and 201. The protection plates 200, 201, mount side by side on the sloped top structure 170 of the receiving structure 100. Each protection plate has a locking mechanism 220 that mates with the sloped top structure 170 of receiving structure 100. In addition, protection plate 200 also has saver sub guides 210, similar to the corner saver sub guides 150 located on the receiving structure 100.

Figure 5:
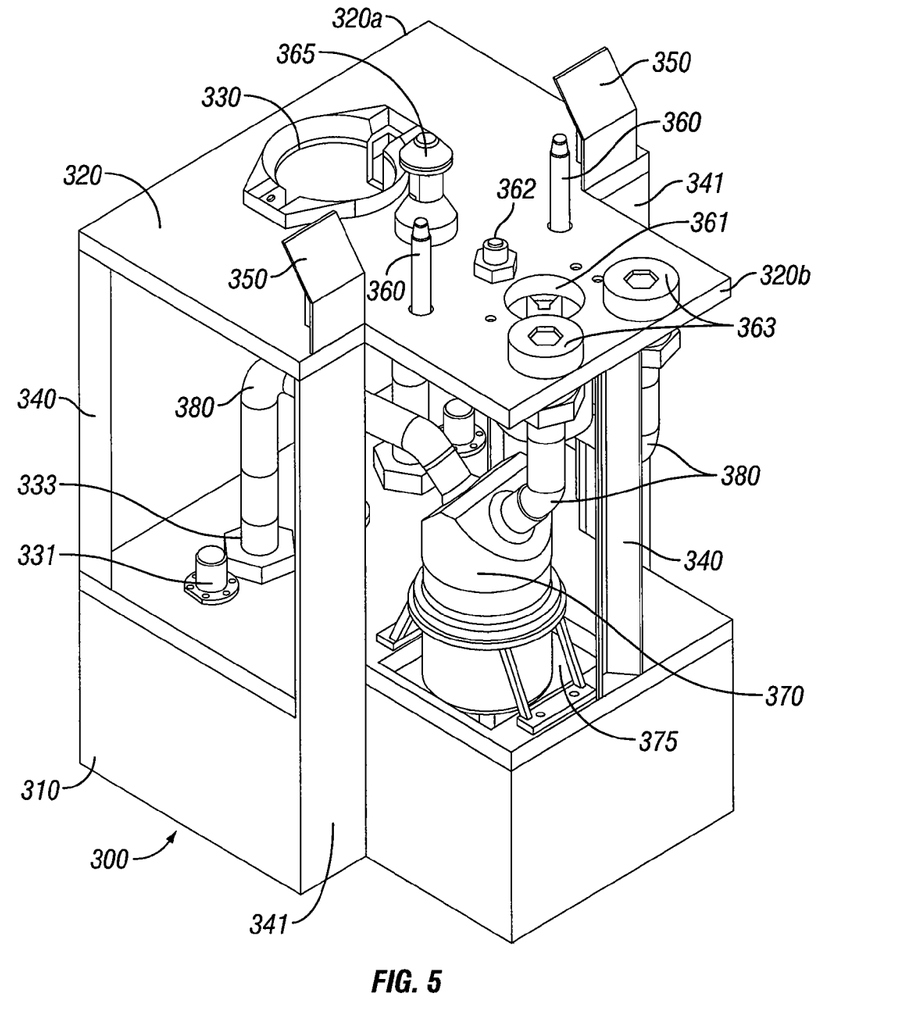
FIGS. 5 and 6 show perspective views of a saver sub in accordance with various embodiments.
Figure 6:
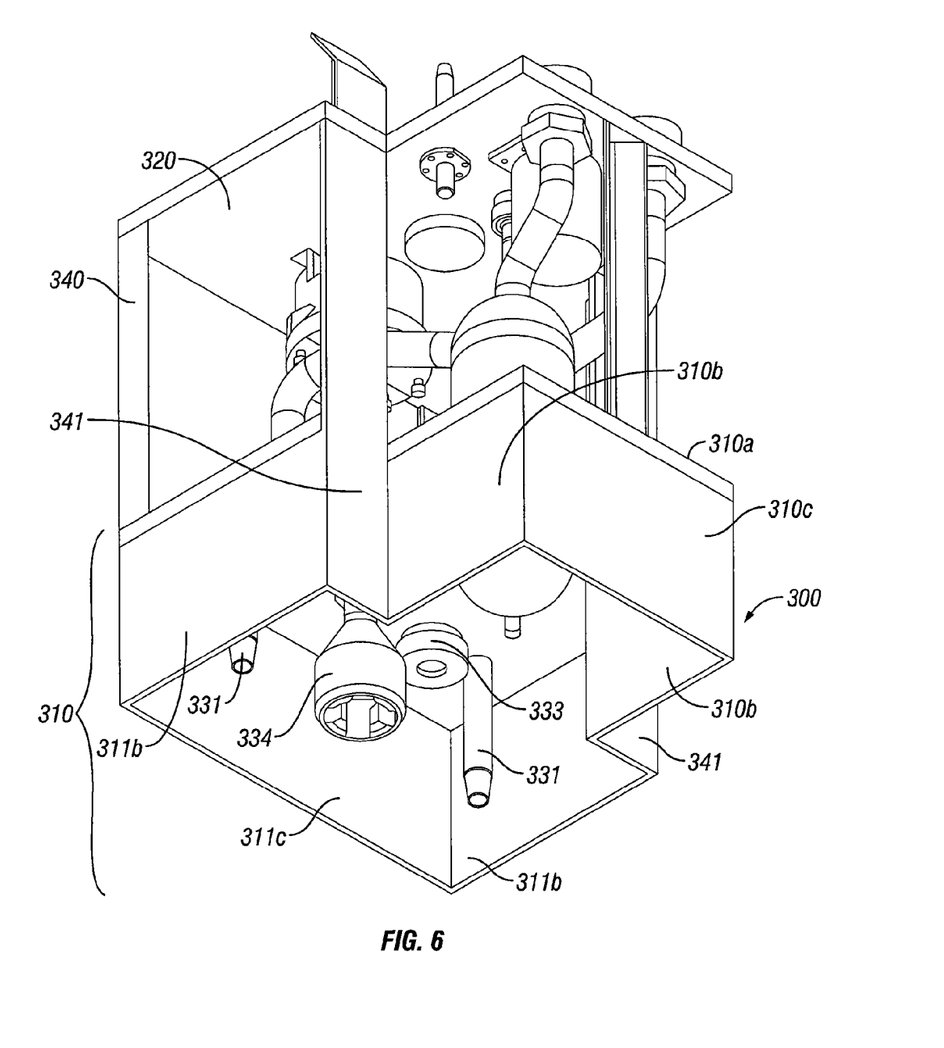

As shown in FIGS. 5 and 6, saver sub 300 includes a base structure 310, a top plate 320, a plurality of posts 340, a three port bottle 370, pipe work 380, and retrievable skid guides 350. The base structure 310 includes a top surface 310a, a plurality of side surfaces 310, and additional couplings and guidance pins to be described in more detail below. The top surface 310a includes notches cut out of two corners, creating indented sides 310b, 341. A hole 375 is cut out of the top surface 310a to allow the three port bottle 370 to sit approximately half above and half below the top surface 310a.

Figure 7:
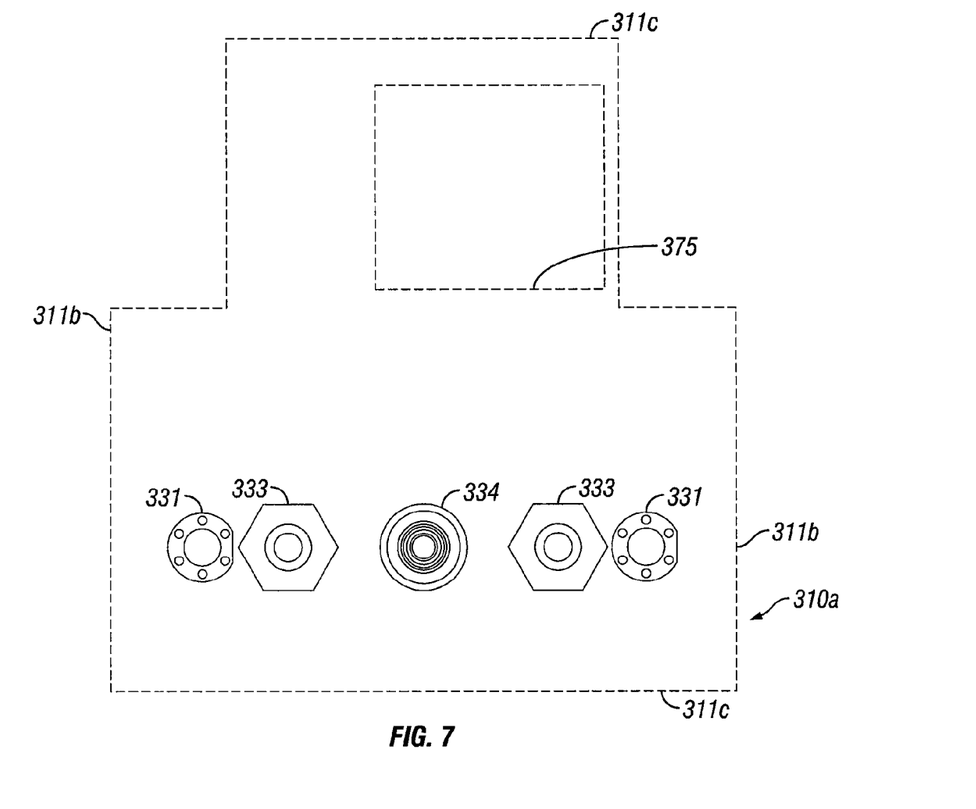
FIG. 7 shows a bottom view of an embodiment of the multiple quick connect components on the saver sub that interface with the receiving structure.

FIG. 7 shows an underside view of the lower surface 311c. The lockdown boss 334 is disposed on the underside of lower surface 311c and connects to the lockdown housing 134 on the receiving structure 100 as shown in FIG. 2. Couplings 333 are spaced from the lockdown boss 334. The couplings 333 interface with the pass through holes 133 on the receiving structure 100, as shown in FIG. 2, and are positioned accordingly. The receiving structure guide pins 331 are disposed on the underside of the lower surface 311c and aid in the proper alignment of the saver sub 300 with the receiving structure 100 during installation. The receiving structure guide pins 331 fit inside the bushing guides 131 shown in FIG. 2.

Figure 8:
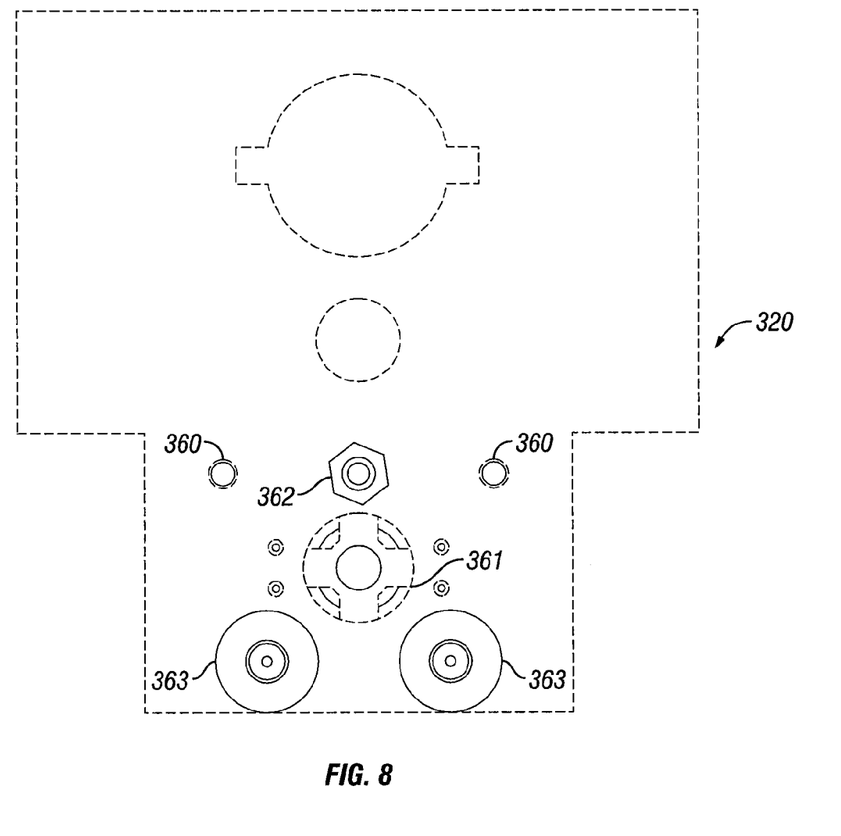
FIG. 8 shows a top view of an embodiment of the multiple quick connect components on the saver sub that interface with the retrievable skid.

FIG. 5 shows a plurality of posts 340 and 341 extending between the base structure 310 to the top plate 320. As shown in FIG. 8, the top plate 320 includes a lockdown bucket 330, a lift mandrel 365, retrievable skid guides 350, and the mating MQC components: two retrievable skid guide pins 360, lockdown boss 361, one half inch coupling 362, and two one inch couplings 363.

The lockdown bucket 330, shown in FIG. 5, serves as the connection point for the ROV to lock the saver sub 300 onto to receiving structure 100 in a method as is known to those skilled in the art. The lockdown bucket 330 includes a releasable connection moveable between a locked and unlocked position and operable by the ROV. The lift mandrel 365 is disposed on the top plate 320 and protrudes above the top plate 320. The lift mandrel 365 includes alternating cylindrical and conical sections, and is engageable by a lifting adapter (not shown) as is known by those skilled in the art. The lower portion of the two retrievable skid plate guides 350 are disposed on the top plate 320 and extend from the surface of the top plate 320 at the two posts 341. The upper portion of the retrievable skid guides 350 is angled to aid the ROV operator to guide the retrievable skid 400 into the receiving structure 100 next to the saver sub 300.

Two couplings 363 are located along top plate 320. The couplings 363 interface with the retrievable skid MQC components (to be described below). The lockdown boss 361 is disposed in the smaller rectangular portion of the top plate 320. The lockdown boss 361 mates with the lockdown boss of the retrievable skid (to be discussed below). The one half inch coupling 362 is disposed on the top plate 320 a distance away from the lockdown boss 361. The coupling 362 also interfaces with the retrievable skid MQC components. The retrievable skid guide pins 360 are disposed away from coupling 362 and engage the bushing guides located on the retrievable skid (to be discussed in greater detail below).

FIG. 5 shows pipe work 380 disposed between the top plate 320 and the base structure 310, which moves fluid between the manifold (not shown) and the retrievable skid 400. The pipe work 380 connects various components; for example, pipe work 380 connects coupling 333 to the three port bottle 370 as well as the three port bottle 370 to the couplings 363.

Figure 11:
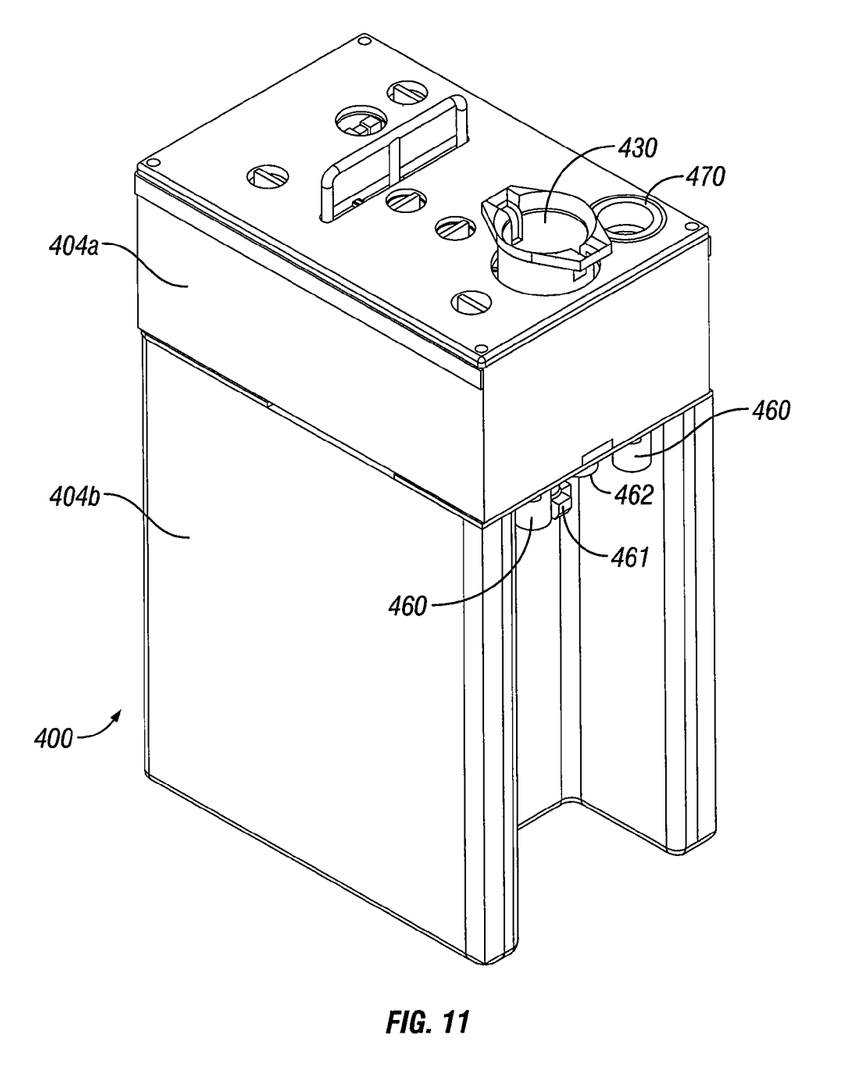
FIG. 11 shows a perspective view of the retrievable skid.

FIG. 11 shows the retrievable skid 400 with buoyancy shells 404a and 404b. The buoyancy shells 404a, 404b are attached to the chassis plate 403 (shown in FIG. 9) and, thus, form part of the structural frame of the retrievable skid 400. The buoyancy shells 404a, 404b also serve to reduce the in-water weight of the retrievable skid 400. However, it should be appreciated by one of skill in the art that the buoyancy shells 404a, 404b are not necessary for the retrievable skid 400.

Figure 9:
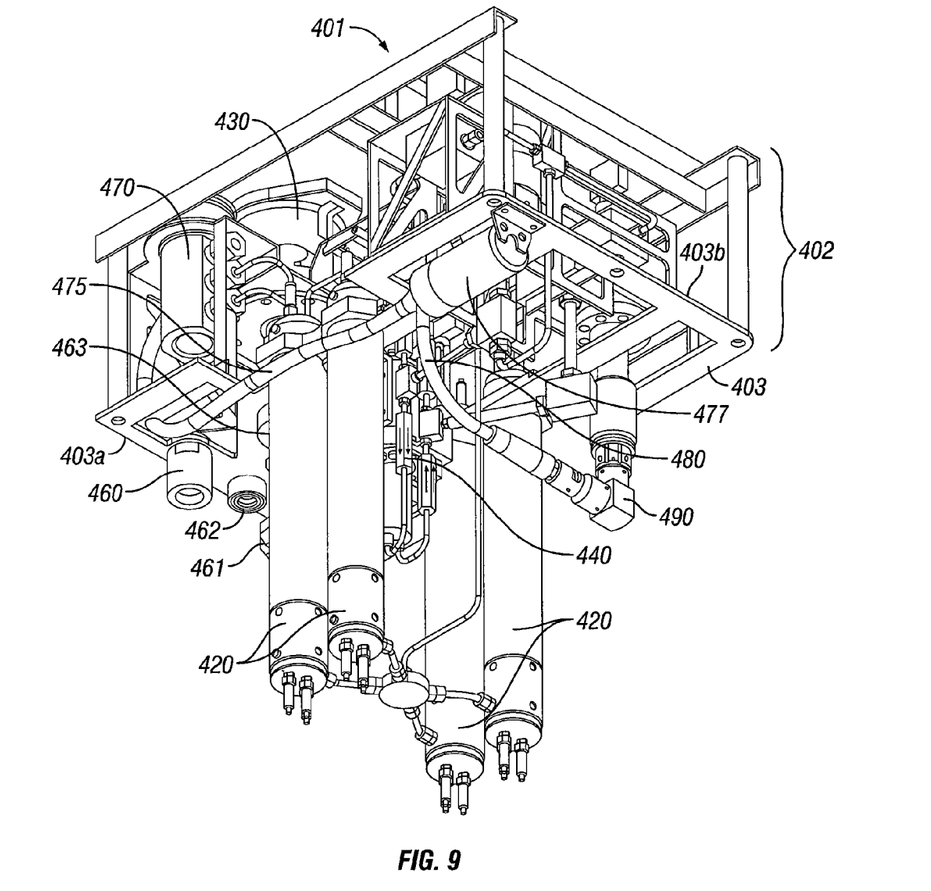
FIG. 9 shows a perspective view of the retrievable skid in accordance with various embodiments.

FIG. 9 shows the retrievable skid 400 without the buoyancy shells. The retrievable skid 401 includes a truss 402, lockdown bucket 430, hotstab 470, pump 440, sample chambers 420 (four are shown), and MQC components: bushing guides 460, couplings 462 and 463, and skid lockdown boss 461. The truss 402 includes a chassis plate 403 with a plurality of cut outs to accommodate the mounting of various retrievable skid components, including the buoyancy shells 404a, 404b shown in FIG. 11. The chassis plate 403 provides the structural support for the retrievable skid 400 and any impact loads received by a retrievable skid component is transferred to the chassis plate 403. A plurality of additional posts also form the truss 402.

The lockdown bucket 430 is disposed on the chassis plate 403 such that the aperture of the lockdown bucket 430 is disposed on the top surface of the truss 402. The lockdown bucket 430, shown in FIG. 11, serves as the connection point for the ROV to lock the retrievable skid 300 onto to the saver sub 300 in a method as is known to those skilled in the art. The lockdown bucket 430 includes a releasable connection moveable between a locked and unlocked position and operable by the ROV.

The aperture of the electro-hydraulic hotstab receptacle 470 (referred to as "hotstab" hereinafter) is similarly disposed on the top surface of the truss 402. The hotstab 470 mates with a hotstab counterpart on the ROV as known to those skilled in the art. The hotstab 470 is used for hydraulic power of the pump 440 and for power and communication for other components, supplied by the ROV (not shown). A flexible hose 475 connects the hotstab the hotstab pod 477. The hotstab pod 477 is connected through the electrical harness 480 and the connector 490 to the sensor which is mounted to the chassis plate 403.

The pump 440, preferably a positive displacement pump, is preferably disposed in approximately the chassis plate 403 and connects to the hotstab 470, the three port bottle 370 of the saver sub 300, and the sample chambers 420. The pump 440 is powered by the hotstab 470 and receives hydraulic power from an ROV (not shown). The pump 440 draws production fluid samples through the three port bottle 370, fills the sample chambers 420, and flushes the system. In a preferred embodiment, the pump 440 has three pumping modes: single phase, multiphase, and flushing.

The sample chambers 420 can be, for example, cylindrical, grouped in a 2×2 matrix formation, and disposed radially on the bottom surface of the chassis plate 403, such that the sample chambers 420 surround the pump 440. Although four sample chambers 420 are shown, any number of sample chambers may be used and positioned in any appropriate configuration. The preferred embodiment of a sample chamber 420 has three separate compartments—one for the fluid sample, one for MEG/water/glycol, and one for nitrogen. Filling the sample chamber 420 with fluid is facilitated by drawing water/glycol from the middle compartment, thus, drawing in the fluid sample. Once the sample chamber 420 is returned to the surface, 10% of the fluid sample is purged. Then the valve that communicates between the water and nitrogen compartments is opened, which allows a gas cap to be introduced to the sample.

Figure 10:
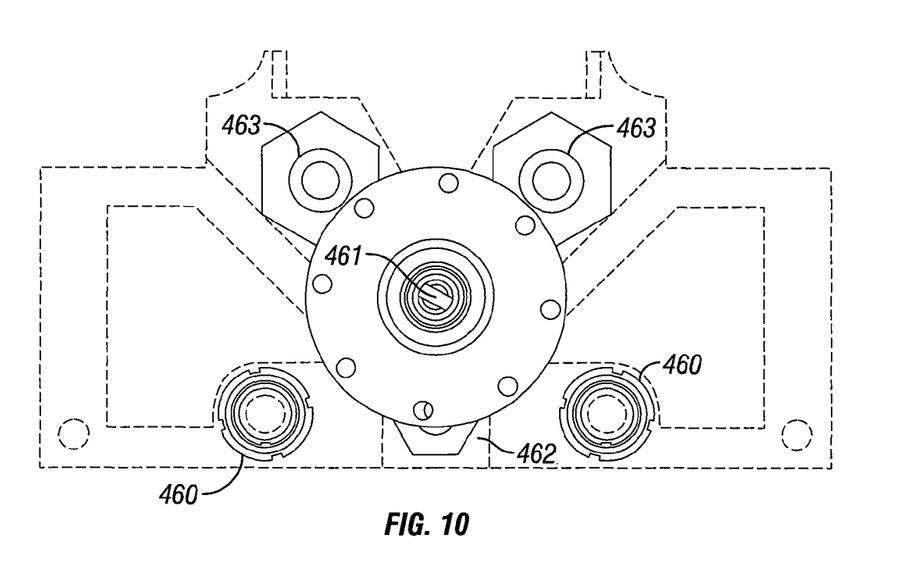
FIG. 10 shows a top view of an embodiment of the multiple quick connect components on the chassis plate of the retrievable skid that interface with the saver sub.

The MQC components are shown in FIG. 10. The bushing guides 460 and the two one inch couplings 463 are disposed on the chassis plate 403. All the couplings 462, 463 extend above and below the surface of the chassis plate 403. The skid lockdown boss 461 also extends above and below the surface of the chassis plate 403. The MQC components on the retrievable skid 400 interface with the upper MQC components of the saver sub 300 in like manner as the lower saver sub MQC components interface with the MQC components of the receiving structure 100.

Figure 12:
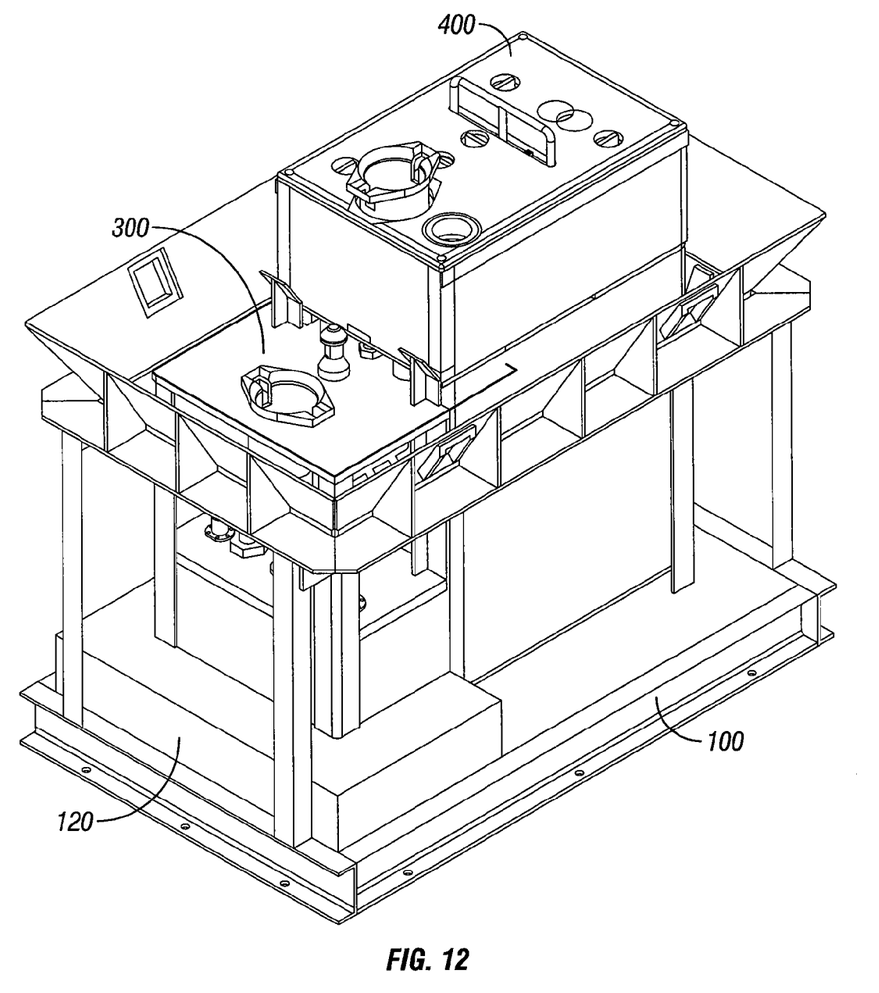
FIG. 12 shows a perspective view of a pump driven sampling assembly in accordance with various embodiments.
Figure 13:
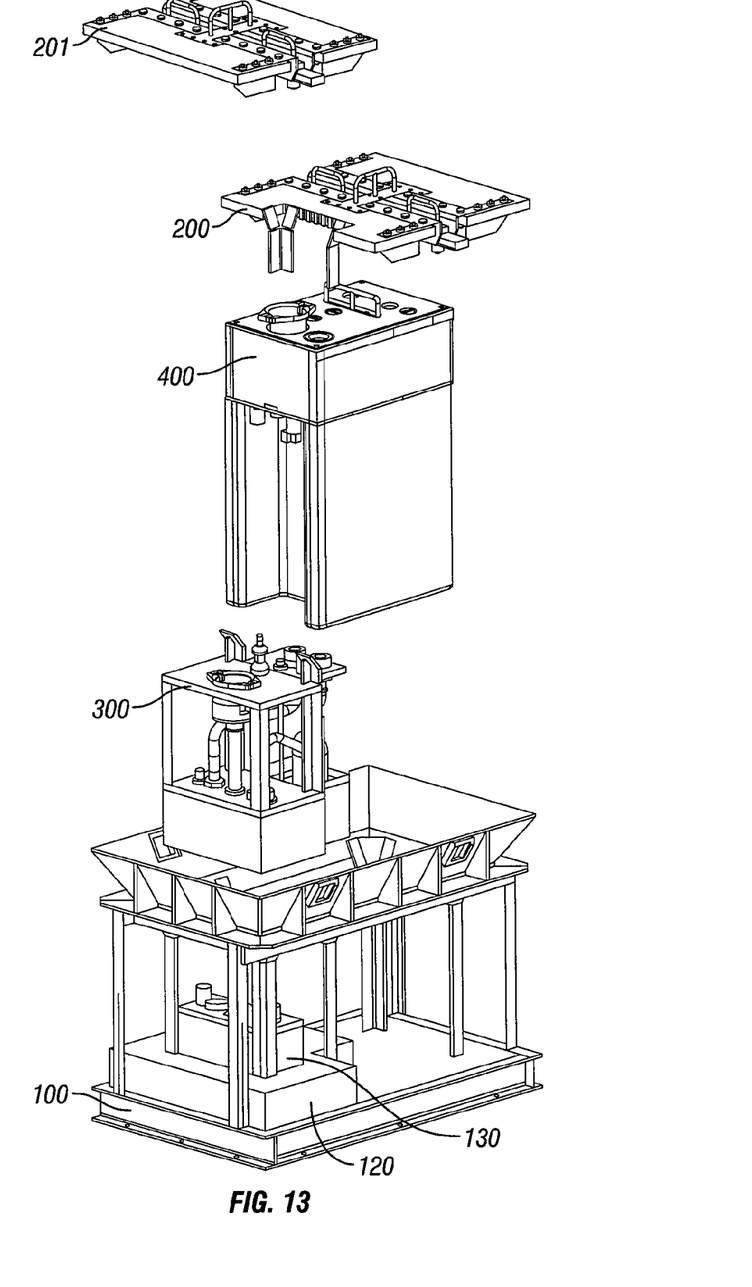
FIG. 13 shows an exploded view of a pump driven sampling assembly.
Figure 15:
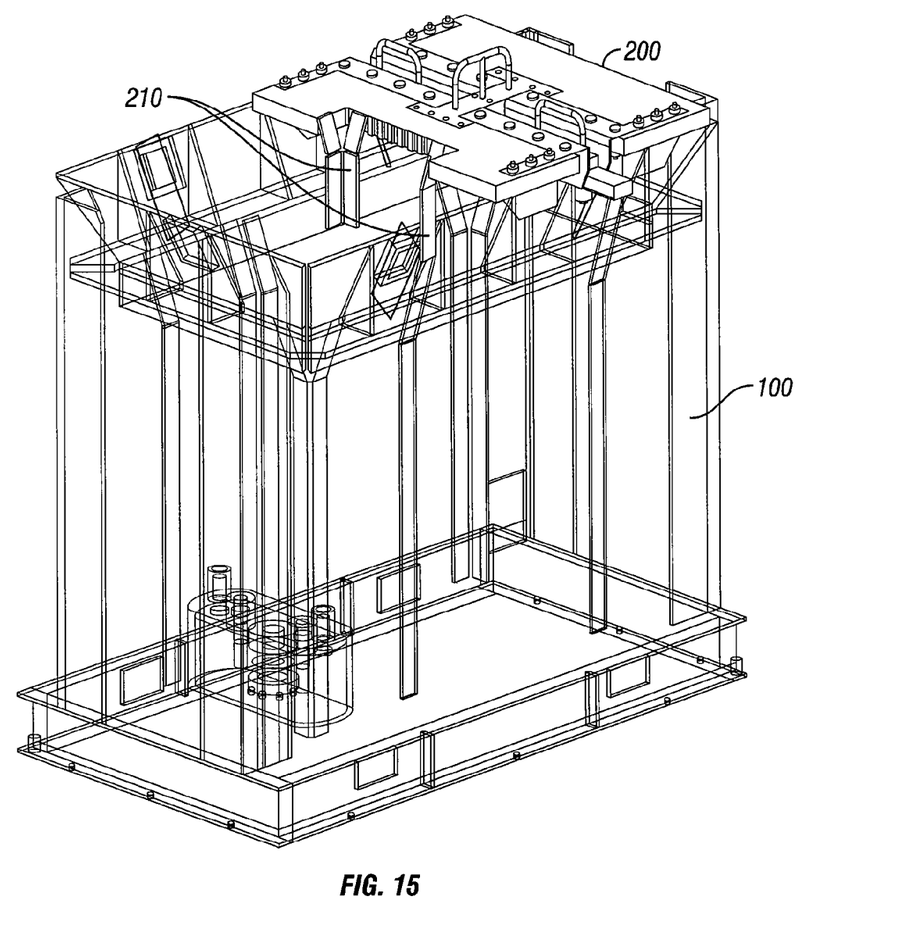
FIG. 15 shows a perspective view of an embodiment of a protection plate mounted on the receiving structure.

FIGS. 12, 13, and 15 show an embodiment for a sampling assembly for sampling production fluids from an oil or gas well. The well includes a structure, such as a manifold, an Xmas tree, or a length of pipe (not shown, generally referred to as "manifold") and a sampling assembly that includes a receiving structure 100, a saver sub 300, a retrievable skid 400, and protection plates 200, 201. The receiving structure 100 is secured to the manifold, from which production fluid samples will be taken. The receiving structure 100 is connected to the production flow in a manner known to those skilled in the art. The receiving structure 100 is considered non-releasably connected to the manifold, preferably welded into place. The connection is designed as a long term, permanent type connection rather than a quick connect/disconnect configuration. Via an ROV, as known to those skilled in the art, the saver sub 300 is guided by and installed on the raised platform 120 of the receiving structure 100. The retrievable skid 400 is installed after the saver sub 300 and is transported and installed via ROV on the receiving structure 100 adjacent to the raised platform 120. In a preferred embodiment, when the saver sub 300 and the retrievable skid 400 are installed in the receiving structure 100, the receiving structure 100 transfers the load from the saver sub 300 and retrievable skid 400 to the manifold.

FIG. 13 depicts the components of the pump driven sampling assembly prior to integration. The saver sub 300 attaches to the receiving structure 100 at the saver sub interface 130 disposed on the raised platform 120. Next, the retrievable skid 400 is placed, by ROV, in the receiving structure 100; the retrievable skid 400 partially overlaps and interfaces with the saver sub 300.

The saver sub 300 accesses the production flow via its MQC connection with the receiving structure 100. The retrievable skid 400 is then connectable to the saver sub 300 with the MQC "quick" connect/disconnect connection. Thus, the receiving structure 100 allows samples to be taken throughout the lifecycle of the manifold and the saver sub 300 reduces the number of makes and breaks on the couplings between the manifold and the receiving structure 100—instead, the interface between the retrievable skid 400 and the saver sub 300, and also possibly the interface between the saver sub 300 and the receiving structure 100, is cycled with every sample taken. This saves the wear and tear on the manifold itself and allows for servicing the receiving structure 100 by replacing the saver sub 300 when needed as opposed to replacing parts on the manifold itself.

FIG. 15 shows the receiving structure 100 with protection plate 200 installed. Prior to the saver sub 300 installation, protection plate 200 is disposed on the receiving structure in the diametrically opposite side from the raised platform 120. Saver sub guides 210 located on protection plate 200 serve to guide the saver sub 300, as shown in FIG. 10, into the proper location over the raised platform 120 and the saver sub interface 130. Both protection plates 200, 201 may be installed when the receiving structure 100 has no components installed or when only the saver sub 300 is installed. Both protection plates 200, 201 are removed to allow for installation of the retrievable skid 400.

Figure 14:
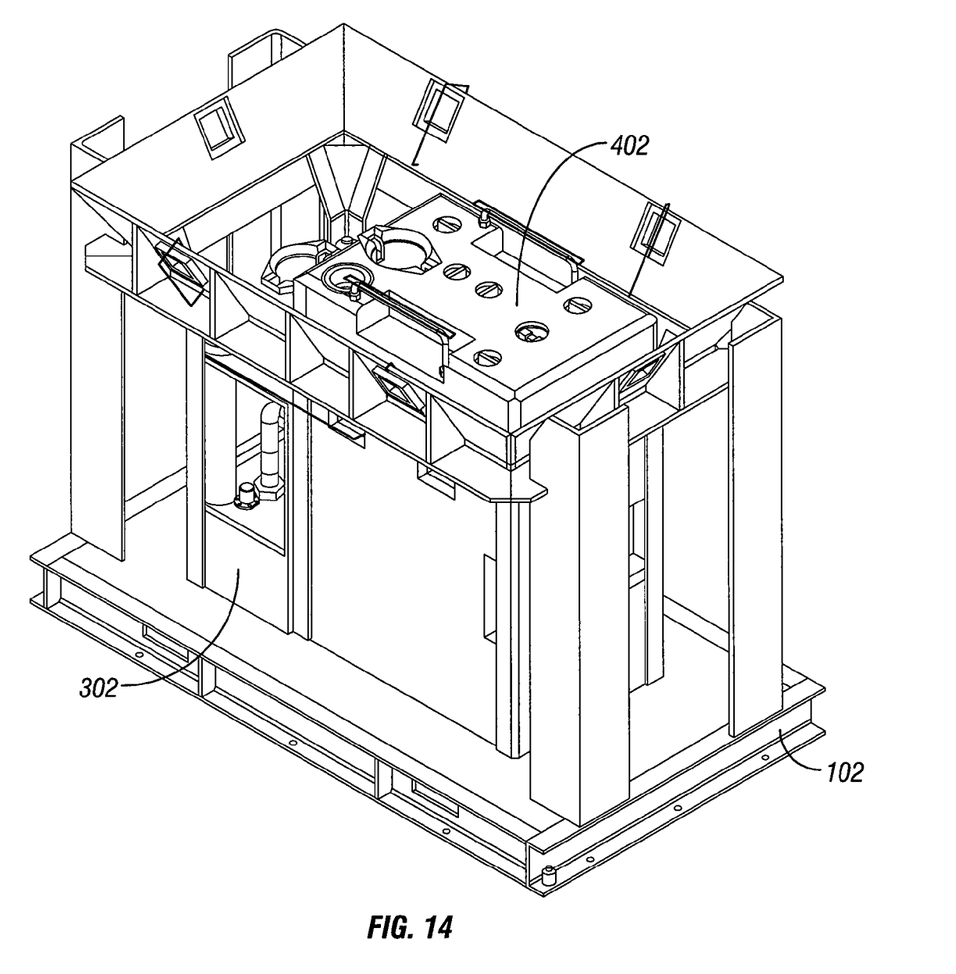
FIG. 14 shows an alternative embodiment of a pump driven sampling assembly.

The retrievable skid 400 shown in FIG. 12 extends above the top of the receiving structure 100. In a preferred embodiment, the retrievable skid 400 can support its own weight and can withstand impacts from the ROV. FIG. 14 shows an alternative embodiment that includes an alternative receiving structure 102, an alternative saver sub 302, and an alternative retrievable skid 402. In this embodiment, the alternative saver sub 302 and alternative retrievable skid 402, when integrated in the alternative receiving structure 102, are fully recessed below the level of the protection plates, 200, 201 as shown in FIG. 14, which reduces potential ROV impacts.

Although the present invention has been described with respect to specific details, it is not intended that such details should be regarded as limitations on the scope of the invention, except to the extent that they are included in the accompanying claims.

What is claimed is:

1. A sampling assembly for taking production fluid samples from a subsea well, including:
    a receiving structure positionable on a subsea structure of the well so as to be in fluid communication with the well production fluid;
    a saver sub positionable upon the receiving structure so as to be in fluid communication with the well production fluid through the receiving structure;
    a retrievable skid removably positionable upon the receiving structure so as to be in fluid communication with the well production fluid through the saver sub; and
    the retrievable skid including a pump and a sample chamber operable to collect a sample of the well production fluids.

2. The sampling assembly of claim 1 further including a plurality of protection plates positionable on the receiving structure.

3. The sampling assembly of claim 2, wherein the saver sub and retrievable skid components are fully recessed below the level of the protection plates.

4. The sampling assembly of claim 1 further including a three port bottle attachably connected to the pump and operable to separate a more dense phase from a less dense phase of the production fluid.

5. The sampling assembly of claim 4, wherein the three port bottle can be removed.

6. The sampling assembly of claim 4, wherein the three port bottle can take single or multiphase fluid flow samples a plurality of times throughout the life of production flow.

7. The sampling assembly of claim 1, including more than one sample chamber and fluid samples are recovered from different wells and retained in separate sample chambers.

8. The sampling assembly of claim 1, wherein a subsea remote operated vehicle (ROV) transports and places the retrievable skid on the receiving structure.

9. The sampling assembly of claim 1, wherein an ROV supplies power to the sampling skid.

10. The sampling assembly of claim 1, wherein a protection plate is used to guide the saver sub onto the receiving structure.

11. The sampling assembly of claim 1, wherein the retrievable skid is placeable onto the receiving structure through the use of a plurality of guides.

12. The sampling assembly of claim 1, wherein the retrievable skid includes outer shells to protect components from ROV impacts and provide buoyancy.

13. The sampling assembly of claim 1, wherein the retrievable skid is releasably connectable with the saver sub with a releasable connection movable between a locked and unlocked position.

14. The sampling assembly of claim 13, wherein the retrievable skid is connectable with the saver sub and the releasable connection movable by the use of an ROV.

15. The sampling assembly of claim 1, wherein the subsea structure includes at least one of a production manifold, an Xmas tree, or a length of pipe.

16. A subsea well for producing production fluid, including:
    a subsea structure attached to the well;
    a subsea sampling assembly, including:
        a receiving structure positionable on the subsea structure so as to be in fluid communication with the well production fluid;
        a saver sub positionable upon the receiving structure so as to be in fluid communication with the well production fluid through the receiving structure;
        a retrievable skid removably positionable upon the receiving structure so as to be in fluid communication with the well production fluid through the saver sub; and
        the retrievable skid including a pump and a sample chamber operable to collect a sample of the well production fluids.

17. The subsea well of claim 16 wherein the sampling assembly further includes:
    a three port bottle attachably connected to the pump operable to separate a more dense phase from a less dense phase of the production fluid; and
    wherein the three port bottle can take single or multiphase fluid flow samples a plurality of times throughout the life of production flow.

18. The subsea well of claim 16, further including more than one subsea well and wherein fluid samples are recovered from the different wells and retained in separate sample chambers.

19. The subsea well of claim 16, wherein a subsea remote operated vehicle (ROV) transports and places the retrievable skid on the receiving structure.

20. The subsea well of claim 16, wherein the retrievable skid is releasably connectable with the saver sub with a releasable connection movable between a locked and unlocked position.

21. The subsea well of claim 20, wherein the retrievable skid is connectable with the saver sub and the releasable connection movable by the use of an ROV.

* * * * *